United States Patent [19]

Zahler et al.

[11] Patent Number: 5,143,913

[45] Date of Patent: Sep. 1, 1992

[54] [3S(Z)]-3-[[(2-AMINO-4-THIAZOLYL)[[2-(HYDROXYAMINO)-2-OXOETHOXY]IMINO]ACETYL]AMINO]-2,2-DIMETHYL-4-OXO-1-AZETIDINYL SULFATE

[75] Inventors: Robert Zahler, Princeton, N.J.; Joseph E. Sundeen, Yardley, Pa.

[73] Assignee: E. R. Squibb & Sons, Inc., Princeton, N.J.

[21] Appl. No.: 700,884

[22] Filed: May 10, 1991

Related U.S. Application Data

[63] Continuation of Ser. No. 177,196, Apr. 4, 1988, abandoned.

[51] Int. Cl.$^5$ .................. A61K 31/425; C07D 417/12
[52] U.S. Cl. ..................... 514/210; 540/355
[58] Field of Search ................. 540/355; 514/210

[56]  References Cited

U.S. PATENT DOCUMENTS

| | | | |
|---|---|---|---|
| 4,252,802 | 2/1981 | Denzel et al. | 424/246 |
| 4,337,197 | 6/1982 | Gordon et al. | 260/239 |
| 4,533,660 | 8/1985 | Gordon et al. | 514/210 |
| 4,638,060 | 1/1987 | Sundeen et al. | 540/203 |
| 4,638,061 | 1/1987 | Slusarchyk et al. | 540/355 |
| 4,684,722 | 8/1987 | Sundeen | 540/203 |
| 4,694,083 | 9/1987 | Slusarchyk et al. | 546/14 |
| 4,743,685 | 5/1988 | Breuer | 540/363 |

OTHER PUBLICATIONS

Brown et al, Chem Abs 110, 132072z (1989).
Summerill, "XXVII Interscience Conf. on Antimicrob. Agents & Chemotherapy", Oct. 23–26, 1988 Abstract 238.
Whitney, "XXVII Interscience Conf. on Antimicrob. Agents & Chemotherapy", Oct. 23–26, 1988 Abstract 239.

*Primary Examiner*—Mark L. Berch
*Attorney, Agent, or Firm*—Timothy J. Gaul

[57] ABSTRACT

The compound [3S(Z)]-3-[[(2-amino-4-thiazolyl)[[2-(hydroxyamino)-2-oxoethoxy]imino]acetyl]amino]-2,2-dimethyl-4-oxo-1-azetidinyl sulfate has gram-positive and gram-negative activity and good oral absorption.

2 Claims, No Drawings

[3S(Z)]-3-[[(2-AMINO-4-THIAZOLYL)[[2-(HYDROXYAMINO)-2-OXOETHOXY]IMINO]ACETYL]AMINO]-2,2-DIMETHYL-4-OXO-1-AZETIDINYL SULFATE

This is a continuation of copending application Ser. No. 177,196 filed on Apr. 4, 1988 now abandoned.

BACKGROUND OF THE INVENTION

U.S. Pat. No. 4,252,802, issued Feb. 24, 1981 describes certain cephalosporin antibiotics having an acylamino substituent of the formula

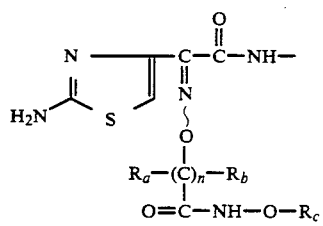

wherein $R_a$ and $R_b$ are independently hydrogen or methyl, $R_c$ is hydrogen, alkyl or alkylphenyl.

U.S. Pat. Nos. 4,337,197, issued Jun. 29, 1982, and 4,533,660, issued Aug. 6, 1985, describe O-sulfated β-lactam hydroxamic acids having antibacterial activity. Preferred compounds, as disclosed in the patents, have the formula

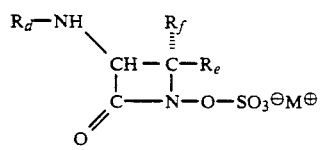

wherein $R_d$ is acyl, $R_e$ and $R_f$ are the same or different and each is hydrogen or alkyl, and $M^+$ is hydrogen or a cation.

U.S. Pat. Nos. 4,638,061, issued Jan. 20, 1987, and 4,694,083, issued Sept. 15, 1987 describe pharmaceutically acceptable salts of [3S(Z)]-2-[[1-(2-amino-4-thiazolyl)-2-[[2,2-dimethyl-4-oxo-1-(sulfooxy)-3-azetidinyl]amino]-2-oxoethylidene]amino]oxy]acetic acid as antibacterial agents, which when compared to other O-sulfated β-lactam hydroxamic acids have superior oral adsorption characteristics in a mammalian host, in conjunction with improved stability to β-lactamase enzymes responsible for β-lactam resistance in the clinic and also improved chemical stability.

U.S. Pat. No. 4,638,060, issued Jan. 20, 1987, describes O-sulfated β-lactam hydroxamic acids having antibacterial activity and having the formula

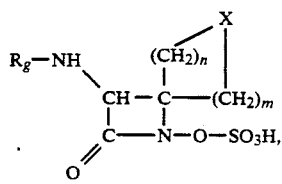

and pharmaceutically acceptable salt thereof, wherein $R_g$ is acyl, and n and m are each independently 1, 2 or 3 and X is a saturated carbon to carbon bond; n and m are each independently 1, 2, 3 or 4, the sum of $n+m \leq 5$ and X is —O—, —S—,

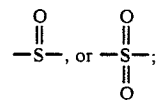

n and m are each independently 1, 2 or 3, the sum of $n+m \leq 4$ and X is

(wherein $R_h$ is alkyl, aryl, hydroxy, alkoxy, alkanoyloxy, carbamoyloxy, alkanoylamino, or ureido) or

(wherein $R_i$ is hydrogen, alkyl, aryl, alkanoyl or carbamoyl); n and m are each independently 1 or 2, the sum of $n+m \leq 3$ and X is

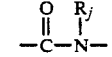

(wherein $R_j$ is hydrogen, alkyl or aryl); or n and m are each 1 and X is —S—CH$_2$—S—,

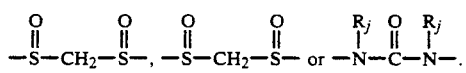

Preferred acyl groups are described as those of the formula

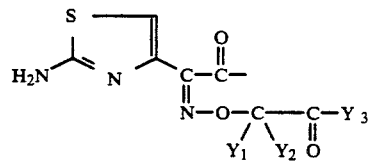

wherein $Y_1$ and $Y_2$ are each independently hydrogen or methyl or $Y_1$ and $Y_2$ together with the carbon atom to which they are attached are cyclopropyl, cyclobutyl or cyclopentyl and $Y_3$ is hydroxy, amino, or hydroxyamino.

U.S. Pat. No. 4,684,722, issued Aug. 4, 1987, describes O-sulfated β-lactam hydroxamic acids having antibacterial activity and having the formula

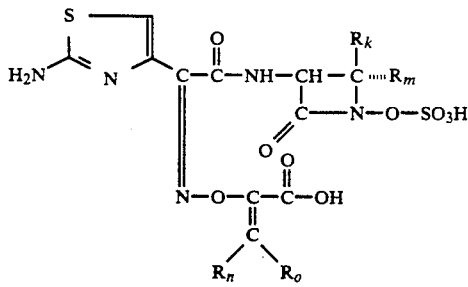

and pharmaceutically acceptable salts thereof, wherein $R_k$ and $R_m$ are the same or different and each is hydrogen or alkyl or $R_k$ and $R_m$ together are $-(CH_2)_n-$ wherein n is 2,3,4 or 5, and $R_n$ and $R_o$ are the same or different and each is hydrogen or alkyl of 1 to 3 carbon atoms.

BRIEF DESCRIPTION OF THE INVENTION

It has been found that [3S(Z)]-3-[[(2-amino-4-thiazolyl)[[2-(hydroxyamino)-2-oxoethoxy]imi no]acetyl]amino]-2,2-dimethyl-4-oxo-1-azetidinyl sulfate, and pharmaceutically acceptable salts thereof, have gram-positive and gram-negative activity and good oral absorption.

DETAILED DESCRIPTION OF THE INVENTION

[3S(E)]-3-[[(2-Amino-4-thiazolyl)[[2-(hydroxyamino)-2-oxoethoxy]imino]acetyl]amino]-2,2-dimethyl-4-oxo-1-azetidinyl sulfate and pharmaceutically acceptable salts thereof, can be used to combat gram-positive and gram-negative infections in mammalian species such as domesticated animals (e.g., dogs, cats, horses and the like) and humans. The compounds are particularly suitable for oral administration, but all modes of administration which have been used in the past to deliver penicillins and cephalosporins to the site of the infection are also contemplated.

For combatting a gram-positive or gramnegative bacterial infection in a mammalian host, [3S(Z)]-3-[[(2-amino-4-thiazolyl)[[2-(hydroxyamino)-2-oxoethoxy]imino]acetyl]amino]-2,2-dimethyl-4-oxo-1-azetidinyl sulfate or a pharmaceutically acceptable salt thereof, can be administered to a mammal in need thereof in an amount effective to treat the infection. The dosage will, of course, depend on the severity of the infection, but will likely be in the range of about 0.5 to about 8 grams per day for a human adult.

For oral administration, [3S(Z)]-3-[[(2-amino-4-thiazolyl)[[2-(hydroxyamino)-2-oxoethoxy]imino]acetyl]amino]-2,2-dimethyl-4-oxo-1-azetidinyl sulfate or a pharmaceutically acceptable salt thereof, can be formulated as a tablet, capsule or solution or suspension in an aqueous vehicle.

The pharmaceutically acceptable salts of this invention include those basic salts formed with inorganic and organic cations. Such salts include ammonium salts, alkali metal salts such as sodium and potassium salts, alkaline earth metal salts such as calcium and magnesium salts and salts derived from organic bases such as dicyclohexylamine, benzathine, hydrabamine, N-methyl-D-glucamine, and choline. Also included within the language "pharmaceutically acceptable salts" are zwitterions (internal or inner salts).

The preparation of the compound of this invention is detailed in the following examples which detail the preparation of the compound as a component of a racemic mixture and as a chiral material.

EXAMPLE 1

[3±(Z)]-3-[[(2-Amino-4-thiazolyl)[[2-(hydroxyamino)-2-oxoethoxy]imino]acetyl]amino]-2,2-dimethyl-4-oxo-1-azetidinyl sulfate

A)

[3±(Z)]-3-[[(2-Amino-4-thiazolyl)[[2-(triphenylmethoxy)amino]-2-oxoethoxy]imino]acetyl]amino]-2,2-dimethyl-4-oxo-1-azetidinyl sulfate, monopotassium salt To a solution of (3±)-3-[(t-butyloxycarbonyl)amino]-4-oxo-2,2-dimethyl-1-azetidinylsulfate, potassium salt (see U.S. Pat. No. 4,638,061, issued Jan. 20, 1987; 174 mg, 0.75 mmole) in dry dichloromethane (1 ml) was added anisole (0.3 ml). After cooling to -10° C. under argon, trifluoroacetic acid (1.3 ml) was added. The reaction mixture was stirred at $-10°$ C. to $-5°$ C. for 1 hour. Toluene was added and the mixture was concentrated at 15° C. in vacuo to a residue. This was triturated twice with hexane to give (3±)-3-amino-4-oxo-2,2-dimethyl-1-azetidinyl sulfate as a white solid which was stored at $-78°$ C. until ready to use.

To a solution of (Z)-2-amino-α-[[[[[[(triphenylmethyl)oxy]amino]carbonyl]methyl]oxy]imino]-4-thiazole acetic acid (251 mg, 0.5 mmole) in 1 ml of dimethylformamide was added triethylamine (50.6 mg, 0.5 mmole). After cooling to $-30°$ C., diphenyl chlorophosphate (134 mg, 0.5 mmole) was added. The reaction mixture was stirred for 1 hour at $-30°$ C. to form the mixed anhydride. (3±)-3-Amino-4-oxo-2,2-dimethyl-1-azetidinylsulfate was dissolved in 1 ml of dimethylformamide and cooled to 0° C. Three equivalents of triethylamine (227 mg, 2.25 mmole) were added to the (3±)-3-amino-4-oxo-2,2-dimethyl1-azetidinylsulfate solution and then the solution was immediately added to the anhydride mixture. After stirring at $-30°$ C. for 15 minutes, the reaction was allowed to slowly warm to $+15°$ C. over a one hour period. The reaction mixture was concentrated in vacuo, dissolved in 40% acetone/water, adjusted to pH 6.5 with 10% potassium bicarbonate, applied to a Dowex AG50 (K+ form) column and eluted with 30% acetone/water. The fractions containing product were concentrated in vacuo to remove the acetone. The aqueous solution was then applied to an HP column and eluted first with water and then with an acetone/water gradient (0–100%). Lyophilization of the fractions containing product yielded 130 mg of the title compound.

B)

[3±(Z)]-3-[[(2-Amino-4-thiazolyl)[[2-(hydroxyamino)-2-oxoethoxy]imino]acetyl]am uino]-2,2-dimethyl-4-oxo-1-azetidinyl sulfate, monopotassium salt

[3±(Z)]-3-[[(2-Amino-4-thiazolyl)[[2-(triphenylmethoxy)amino]-2-oxoethoxy]imino]ace tyl]amino]-2,2-dimethyl-4-oxo-1-azetidinyl sulfate, monopotassium salt (114 mg) was dissolved in 2 ml of water and cooled in an ice/water bath. Cold 98% formic acid (8 ml) was added. After stirring for 15 minutes at 0–5° C., the solution was concentrated in vacuo to a residue and then dissolved in cold water and adjusted to pH 6.5 with 10% potassium bicarbonate. An HP20 column was run, eluting with water. Fractions containing product were combined and lyophilized to give 43 mg of the title compound.

EXAMPLE 2

[3S(Z)]-3-[[(2-Amino-4-thiazolyl)[2-(hydroxyamino)-2-oxoethoxy]imino]acetyl]amino]-2,2dimethyl-4-oxo-1-azetidinyl sulfate, monopotassium salt

Process 1

A solution of [3S(Z)-[[[1-(2-amino-4-thiazolyl)-2-[[2,2-dimethyl-4-oxo-1-(sulfoo xy)-3-azetidinyl]amino]-2-oxoethylidene]amino]oxy]acetic acid (See U.S. Pat. No. 4,638,061, issued Jan. 20, 1987; 1.30 g, 2.97 mmol) and tributylamine (0.55 g, 2.97 mmol) in dimethylformamide (25 ml) was cooled to 0° C., and N-hydroxybenzotriazole (0.40 g, 2.97 mmol) and dicyclohexylcarbodiimide (0.66 g, 3.27 mmol) were added. The mixture was stirred at 0° C. for one hour, and a solution of hydroxylamine-hydrochloride (0.21 g, 2.97 mmol) and tributylamine (0.55 g, 2.97 mmol) in dimethylformamide (20 ml) was added dropwise. The resulting mixture as stirred overnight at room temperature and the dicyclohexyl urea filtered off. The filtrate was evaporated in vacuo and the residue dissolved in acetone. To this solution was added potassium perfluorobutane sulfonate (1.01 g, 2.97 mmol) and the precipitate filtered off by suction. The crude material was purified by medium pressure liquid chromatography on XAD* (water-acetonitrile 95:5) to afford 280 mg of the desired product. This material was further purified by a second medium pressure liquid chromatography on XAD using water as eluent. The product-containing fractions were freeze-dried.

* XAD Adsorbent, research grade type 2 particular size: 0.05–0.1 mm Serva (Heidelberg, West Germany)

Yield: 130 mg with an H.I. of 96.9% and 50 mg with an H.I. of 98.4% melting point: >200° C. (dec.)

IR (KBr): 1770 cm$^{-1}$

NMR (DMSO-d$_6$): δ = 1.26 (s, 3H); 1.40 (s, 3H); 4.47 (s,2H); 4.62 (d, 1H); 6.80 (s, 1H); 7.25 (s, 2H); 9.0 (s, 1H); 9.52 (d, 1H); 10.28 (br., 1H) ppm.

Process 2

A solution of [3S(Z)-[[[1-(2-amino-4-thiazolyl)-2-[[2,2-dimethyl-4-oxo-1-(sulfoo xy)-3-azetidinyl]amino]-2-oxoethylidene]amino]oxy]-acetic acid (21.87 g, 0.05 mol) and n-tributylamine (9.27 g, 0.05 mol) in dimethylformamide (350 ml) was cooled at 0° C. and N-hydroxybenzotriazole (6.76 g, 0.05 mol) and dicyclohexylcarbodiimide (12.20 g, 0.06 mol) were added. The mixture was stirred for one hour at 0° C. and a solution of 2-aminooxy-2-methoxypropane (6.31 g, 0.06 mol) in dimethylformamide (100 ml) was added dropwise. The reaction mixture was stirred overnight at room temperature and the precipitate (dicyclohexyl urea) filtered off by suction. The filtrate was evaporated in vacuo and the residue dissolved in acetone (100 ml). After the addition of potassium perfluorobutane sulfonate (16.91 g, 0.05 mol) and ether (800 ml) crude product precipitated. The precipitate was filtered off, washed with ether, and dried in vacuo. The crude compound (28.76 g) was purified in six portions by medium pressure liquid chromatography on XAD using water as eluent.

Yield: 8.76 g H.I. (HPLC): 91.1–93.0% (average H.I.: 92.0%). Altogether, 22.78 g of product with an H.I. of 91.8% was prepared.

This material was further purified in eight portions by a second medium pressure liquid chromatography on XAD (water). In order to get a uniform batch, the eight different batches were combined, dissolved in water (500 ml), freezedried, triturated with ether, filtered, washed with ether, and dried in vacuo. Yield: 16.0 g, H.I. (HPLC): 97.2% (1% dimethylformamide, 0.2% N-hydroxybenzotriazole. Melting point >168° C. (dec.).

What is claimed is:

1. [3S(Z)]-3-[[(2-amino-4-thiazolyl)[[2-(hydroxyamino)-2-oxoethoxy]imino]acetyl]amino ]-2,2-dimethyl-4-oxo-1-azetidinyl sulfate, or a pharmaceutically acceptable salt thereof.

2. A method of treating a gram-positive or gram-negative bacterial infection in a mammalian host which comprises administering to said host an effective amount of [3S(Z)]-3-[[(2-amino-4-thiazolyl)[2-(hydroxyamino)-2-oxoethoxy]iminoacet yl]amino]-2,2-dimethyl-4-oxo-1-azetidinyl sulfate, or a pharmaceutically acceptable salt thereof.

* * * * *